(12) United States Patent
Schramm et al.

(10) Patent No.: US 7,601,812 B2
(45) Date of Patent: Oct. 13, 2009

(54) IMMUNOMODULATING AGENTS FROM PARASITIC WORMS AND METHOD FOR ISOLATION THEREOF

(75) Inventors: Gabriele Schramm, Sülfeld (DE); Helmut Haas, Sülfeld (DE); Franco Falcone, Nottingham (GB); Achim Gronow, Steinburg (DE); Karin Haisch, GrossNiendorf (DE)

(73) Assignee: Forschungszentrum Borstel Zentrum fur Medizin und Biowissenschaften (DE)

( * ) Notice: Subject to any disclaimer, the term of this patent is extended or adjusted under 35 U.S.C. 154(b) by 632 days.

(21) Appl. No.: 10/469,499

(22) PCT Filed: Mar. 1, 2002

(86) PCT No.: PCT/EP02/02228

§ 371 (c)(1),
(2), (4) Date: Jul. 23, 2004

(87) PCT Pub. No.: WO02/085930

PCT Pub. Date: Oct. 31, 2002

(65) Prior Publication Data

US 2004/0253709 A1     Dec. 16, 2004

(30) Foreign Application Priority Data

Mar. 1, 2001 (DE) .................. 101 09 844

(51) Int. Cl.
*C07K 14/47* (2006.01)
*C12N 15/09* (2006.01)
*C12N 15/64* (2006.01)
*C12P 21/02* (2006.01)

(52) U.S. Cl. ............... 530/351; 435/69.1; 435/70.1; 435/325; 435/471; 435/320.1; 536/23.5

(58) Field of Classification Search ............... None
See application file for complete search history.

(56) References Cited

FOREIGN PATENT DOCUMENTS

WO    WO 02/085930    10/2002

OTHER PUBLICATIONS

Haisch et al. Parasite Immunology, vol. 23, pp. 427-434, 2001.*
Schramm et al. All of Abstracts for Sydney 2000.*
Dunne et al. Trans R Soc Trop Med Hyg. 1981, pp. 54-71.*
Kips et al. European Respiratory Journal. 2001. vol. 17, pp. 499-506.*
Sambrook et al. Molecualr cloning, a laboratory Manual, 2nd edition, pp. 16.17-16.31, 1989.*
Crystal, R. Science, 1995, vol. 270, pp. 404-410.*
Verma et al. Nature, 1997, vol. 389, pp. 239-242.*
Marshall, Science, 1995, vol. 269, pp. 1050-1054.*
Rubanyi, Molecualr Aspects of Medicine, 2001, vol. 22, pp. 113-142.*
Juengst, British Medical Journal, 2003, vol. 326, pp. 1410-1411.*
Boros et al., "Delayed hypersensitivity-type granuloma formation and dermal reaction induced and elicited by a soluble factor isolated from *Schistosoma mansoni* eggs," *J. Exp. Med.* 132:488-507 (1970).
Carter et al., "An electrophoretic analysis of *Schistosoma mansoni* soluble egg antigen preparation," *J. Parasitol* 64:385-390 (1978).
Okano et al., "Induction of Th2 responses and IgE is largely due to carbohydrates functioning as adjuvants on *Schistosoma mansoni* egg antigens," *J. Immunol.* 163:6712-6717 (1999).
Okano et al., "Lacto-N-fucopentaose III found on *Schistosoma mansoni* egg antigens functions as adjuvant for proteins by inducing Th2-type response," *J Immunol.* 167:442-450 (2001).
Patella et al., Endogenous superallergen protein Fv induces IL-4 secretion from human Fc epsilon RI+ cells through interaction with the VH3 region of IgE, *J. Immunol.* 161:5647-5655 (1998).
Patella et al., "HIV-1 gp 120 induces IL-4 and IL-13 release from human Fc epsilon RI+ cells through interaction with the VH3 region of IgE," *J. Immunol.* 164:589-595 (2000).
Pearce, et al., "Downregulation of Th1 cytokine production accompanies induction of Th2 responses by a parasitic helminth, *Schistosoma mansoni*," 173:159-166 (1991). *J. Exp. Med.*
Scott et al., "The role of T-cell subsets and cytokines in the regulation of infection," *Immunol. Today* 12:346-348 (1991).
Vella et al., CD4+ Th2 response induced by *Schistosoma mansoni* eggs develops rapidly, through an early, transient, Th0-like stage, *J. Immunol.* 148:2283-2290 (1992).
Velupillai et al., "Oligosaccharide-specific induction of interleukin 10 production by B220+ cells from schistosome-infected mice: a mechanism for regulation of CD4+ T-cell subsets," *Proc. Natl. Acad. Sci. USA* 91:18-22 (1994).
D. W. Dunne et al., "The stage-, strain- and species-specificity of a *Schistosoma mansoni* egg antigen fraction (CEF6) with serodiagnostic potential," Transactions of the Royal Society of Tropical Medicine and Hygiene (1984) 78, 460-470.
D. W. Dunne et al., "The purification, characterization, serological activity and hepatotoxic properties of two cationic glycoproteins ($\alpha_1$ and $\omega_1$) from *Schistosoma mansoni* eggs," Parasitology (1991), 103, 225-236.
McLaren et al., "Serodiagnosis of human *Schistosoma mansoni* infections: enchanced sensitivity and specificity in ELISA using a fraction containing *S. mansoni* egg antigens $\omega_1$ and $\alpha_1$," Transactions of the Royal Society of Tropical Medicine and Hygeine, vol. 75, No. 1, 1981.
Schramm et al., "IPSE/alpha-1: A major immunogenic component secreted from *Schistosoma mansoni* Eggs," Molecular & Biochemical Parasitology 147 (2006) 9-19.

* cited by examiner

*Primary Examiner*—Bridget E Bunner
*Assistant Examiner*—Fozia M Hamud
(74) *Attorney, Agent, or Firm*—Ballard Spahr Andrews & Ingersoll, LLP (57) ABSTRACT

The invention relates to active agents from parasitic worms, in particular *Schistosoma mansoni*, which induce a T-helper type 2 response (Th2 immune response).

21 Claims, 2 Drawing Sheets

```
            9          18          27          36          45          54
5' ATG TTT CFT ATT GCC GTA TTG TCA TAC ACA TTG ATA AGT CAA TTG GGG ATA ACT
   --- --- --- --- --- --- --- --- --- --- --- --- --- --- --- --- --- ---
   M   F   L   I   A   V   L   S   Y   T   L   I   S   Q   L   G   I   T 63          72          81          90          99         108
   ACA TCG GAT TCA TGC AAA TAT TGT CTA CAA TTG TAC GAT GAA ACG TAT GAG AGG
   --- --- --- --- --- --- --- --- --- --- --- --- --- --- --- --- --- ---
   T   S   D   S   C   K   Y   C   L   Q   L   Y   D   E   T   Y   E   R 117         126         135         144         153         162
   GGT TCA TAT ATT GAA GTC TAC AAA AGC GTT GGC TCA CTC TCA CCA CCA TGG ACA
   --- --- --- --- --- --- --- --- --- --- --- --- --- --- --- --- --- ---
   G   S   Y   I   E   V   Y   K   S   V   G   S   L   S   P   P   W   T 171         180         189         198         207         216
   CCT GGA TCT GTT TGT GTA CCC TTC GTA AAT GAC ACG AAG AGA GAG CGT CCA TAC
   --- --- --- --- --- --- --- --- --- --- --- --- --- --- --- --- --- ---
   P   G   S   V   C   V   P   F   V   N   D   T   K   R   E   R   P   Y 225         234         243         252         261         270
   TGG TAT TTA TTT GAC AAC GTC AAT TAC ACA GGT CGG ATT ACT GGT CTC GGA CAT
   --- --- --- --- --- --- --- --- --- --- --- --- --- --- --- --- --- ---
   W   Y   L   F   D   N   V   N   Y   T   G   R   I   T   G   L   G   H 279         288         297         306         315         324
   GGT ACC TGC ATT GAT GAC TTC ACG AAA TCC GGA TTC AAA GGC ATT TCC TCT ATT
   --- --- --- --- --- --- --- --- --- --- --- --- --- --- --- --- --- ---
   G   T   C   I   D   D   F   T   K   S   G   F   K   G   I   S   S   I 333         342         351         360         369         378
   AAA CGG TGT ATT CAA ACA AAG GAT GGA AAA GTT GAA TGT ATC AAT CAA CCG AAA
   --- --- --- --- --- --- --- --- --- --- --- --- --- --- --- --- --- ---
   K   R   C   I   Q   T   K   D   G   K   V   E   C   I   N   Q   P   K 387         396         405
   CGG AGA AGG ACA TAC TGT CGA TTC TAA 3'
   --- --- --- --- --- --- --- --- ---
   R   R   R   T   Y   C   R   F   *
```

IMMUNOMODULATING AGENTS FROM PARASITIC WORMS AND METHOD FOR ISOLATION THEREOF

This application is the National Stage of International Application No. PCT/EP02/02228, filed Mar. 1, 2002, which is incorporated herein by reference in its entirety and which claims priority under 35 U.S.C. § 119(a) to German Patent Application No. DE10109844.8, filed Mar. 1, 2001, which is incorporated herein by reference in its entirety.

BACKGROUND OF THE INVENTION

In a number of diseases, a pathological Th1 or an attenuated Th2 reaction has been causally demonstrated or these reactions are the subject of discussion. Findings from animal experiments give rise to the supposition that a change in immune response towards Th2 has a protective effect in these diseases. Organ-specific autoimmune diseases such as the following may be cited in this context: multiple sclerosis [Shevach, E. M. et al., *Springer Semin. Immunopathol.* 21 (1999) 249-262; Leonard, J. P. et al., *Crit. Rev. Immunol.* 17 (1997) 545-553], autoimmune uveitis [Singh, V. K. et al., *Immunol. Res.* 20 (1999) 147-161; Sun, B. et al., *Int. Immunol.* 11 (1999) 1307-1312; Egwuagu, C. E. et al., *J. Immunol.* 162 (1999) 510-517], insulin-dependent diabetes mellitus [Rabinovitch, A. et al., *Biochem. Pharmacol.* 55 (1998) 1139-1149; Cooke, A. et al., Parasite Immunol. 21 (1999) 169-176], rheumatoid arthritis [Muller, B. et al., Springer *Semin. Immunopathol.* 20 (1998) 181-196], Behçet's syndrome [Frassanito, M. A. et al., *Arthritis Rheum.* 42 (1999) 1967-1974] and furthermore *Helicobacter pylori* infection (the cause of, among other things, gastric ulcer and atrophic gastritis) [Smythies, L. E. et al., *J. Immunol.* 165 (2000) 1022-1029; Fox, J. G. et al., *Nat. Med.* 6 (2000) 536-542; Mattapallil, J. J. et al., *Gastroenterology* 118 (2000) 307-315], inflammatory intestinal diseases such as Crohn's disease and others [Romagnani, P. et al., *Curr. Opin. Immunol.* 9 (1997) 793-799; MacDonald, T. T., *Curr. Top. Microbiol. Immunol.* 236 (1999) 113-135], acute organ transplant rejection reaction [Morelli, A. E. et al., *Transplantation* 69 (2000) 2647-2657] and spontaneous recurrent abortions (Jenkins, C. et al., *Fertil. Steril.* 73 (2000) 1206-1208].

Figure 1:
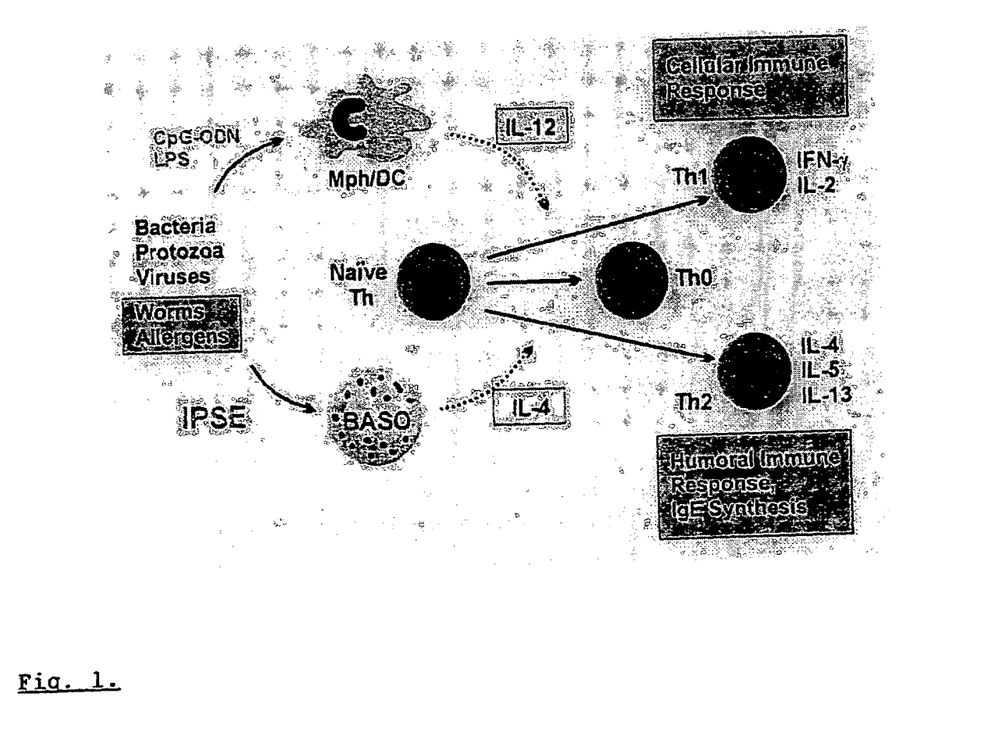
FIG. 1 shows initiation of the Th1 and Th2 immune responses.

In relation to initiation of Th1 and Th2 response, cytokines are regarded as key factors [Paul, W. E. et al., *Cell* 76 (1994) 241-251], with IL-4 probably representing the decisive cytokine signal for the differentiation of naïve T-helper cells into T2 cells. The initiation of a Th1 response is on the other hand controlled essentially by IL-12 and IFN-γ, which are produced by dendritic cells and other accessory cells. Apart from cytokines, other factors may also influence T-cell differentiation [Constant, S. L. et al., *Annu. Rev. Immunol.* 15 (1997) 297-322]. For initiation, IL-4 or IL-12 must be present by the time of priming, i.e. early during an immune response (cf. FIG. 1).

The early production of IL-4 or IL-12 and thus T-cell differentiation are controlled by exogenous and endogenous factors. Among the exogenous factors, the nature of the pathogen is particularly important. A number of pathogens preferentially stimulate a Th1, others a Th2 response [Scott, P. et al., *Immunol. Today* 12 (1991) 346-348]. This gives rise to the supposition that molecular properties of the corresponding pathogen are responsible for the effect in question. As the nature of the pathogen decisively influences early cytokine production, the fundamental question arises as to what the molecular trigger factors are that induce early IL-4 or early IL-12, and what the cellular source is that provides these cytokines.

The cellular source for early IL-4 is the subject of controversy [Coffman, R. L. et al., *J. Exp. Med.* 185 (1997) 373-375]. In principle, several cell types are capable of producing IL-4 if appropriately stimulated: type 2 T cells, murine NK1.1$^+$ T cells, eosinophils, mast cells and basophils. During a primary immune response, early IL-4 very probably originates from cells of the innate immunity, since mature antigen-specific T cells are not yet available at the time of first contact with an immunogen. Even in cases of pre-existing cross-reactive Th2 cells, the question remains as to what structure their development has produced. Type 2 T cells are therefore to be ruled out as the source of early IL-4. The postulated exclusive role of NK1.1$^+$ T cells as the supplier of early IL-4 in the mouse has been called into question by experiments with genetically deficient animals [Coffman, R. L. et al., *J. Exp. Med.* 185 (1997) 373-375].

Various authors have suspected that basophils are involved in the development of a Th2 response [Paul, W. E. et al., *Cell* 76 (1994) 241-251; Romagnani, S., *Immunol. Today* 13 (1992) 379-381; Dahinden, C. A., *Int. Arch. Allergy Immunol.* 113 (1997) 134-137]. In support of this suspicion is the fact that human basophils release considerable quantities of IL-4 within a few hours following antigen-specific and non-specific stimulation [Brunner, T. et al., *J. Exp. Med.* 177 (1993) 605-611; Kasaian, M. T. et al., *Int. Immunol.* 8 (1996) 1287-1297]. In addition, basophils may, as mobile cells of peripheral blood, accumulate rapidly at sites of conflict with pathogens. Migration and accumulation are controlled by a number of chemokines. Eotaxin, which attracts basophils, eosinophils and Th2 cells by binding to their chemokine receptor CCR3, should be emphasised in particular. Interestingly, IL-4 leads to the release of eotaxin from human skin fibroblasts and endothelial cells, which probably represents an amplification mechanism for the recruitment of basophils. In addition to its chemotactic action, eotaxin clearly intensifies antigen-induced IL-4 release from basophils. Compared with basophils, IL-4 production by mast cells and eosinophils is low, which puts their role in Th2 induction into context. In summary, principally basophils are thus considered as producers of early Il4.

The question of the trigger factors for early IL-4 has to date not been definitely answered. For early IL-12, on the other hand, triggering factors are already known. Thus, for example, bacterial products such as lipopolysaccharide and CpG-oligodesoxynucleotides, may induce macrophages or dendritic cells to rapidly release IL-12 and bring about Th1 induction in vivo [Paul, W. E. et al., *Cell* 76 (1994) 241-251; Bohle, B. et al., *Eur. J. Immunol.* 29 (1999) 2344-2353]. The identification of factors for Th2 induction has still to be carried out. However, potential trigger factors that induce rapid IL-4 release from basophils in vitro have already been described: the B cell superantigens protein Fv [Patella, V. et al., *J. Immunol.* 161 (1998) 5647-5655] and HIV glycoprotein 120 [Patella., V et al., *J. Immunol.* 164 (2000) 589-595], which become active by binding to the VH3 segment of IgE, and lectins [Haas, H. et al., *Eur. J. Immunol.* 29 (1999) 918-927], which bind to the carbohydrate side chains of IgE or the IgE receptor.

For the therapy of certain diseases, it would be desirable to direct the immune response towards a type 2 T-helper cell response (Th2 response). There have to date not been satisfactory possibilities for this, and the administration of IL-4 as such is not practicable for routine use as it is too costly and expensive.

The object of the present invention is therefore to make available highly potent Th2 inducers and medicaments for immunomodulation.

This object is achieved according to the invention by new proteins that are isolated from parasitic worms.

Parasitic worms can essentially be classified into three major taxonomic groups of helminths (zestodes, trematodes and nematodes) and are characterised by a parasitic mode of living within vertebrates and/or invertebrates. There, they attack specific organs/tissues: the lumen of the bowels (intestinal nematodes), epithelia (lungworms), blood vessels (schistosomes), lymph vessels and skin (filariae) and various body tissues (larval stages of tapeworms) and are in this connection confronted with differing immunological conditions.

Worldwide, around 3.5 billion people are infected with parasitic worms. Even though direct mortality is low, those affected may experience considerable failure to grow, developmental and organ damage and often chronic disease.

The most important representatives of parasitic worms in humans: the intestinal large round worm (*Ascaris lumbricoides*; around 1 billion people infected), hookworms (*Ankylostoma duodenale* and *Necator americanus*; nearly 1 billion), whipworm (*Trichuris trichiura*; around 800 million), schistosomes (around 200 million), filariae (*Brugia, Onchocerca* and *Wuchereria*, around 100 million) and tapeworm species (*Taenia*; around 50 million).

In animals, infection with parasitic worms, of which there are very many different types, is far greater than in humans. The economic damage inflicted on farm animals can be substantial.

The invention is based on the finding that above all parasitic worms reliably induce a Th2 response. In this context, the property of Th2 induction may be limited to a specific stage of development. Thus, in the case of infection of mice with the trematode *Schistosoma mansoni*, the egg stage induces a Th2-type immune response, while the schistosomula (larval) stage induces a Th1-type immune response [Pearce, E. J. et al., *J. Exp. Med.* 173 (1991) 159-166]. The IL-4-inducing capacity of schistosome eggs is so pronounced that even naïve mice respond to the administration of schistosome eggs following a transient Th0 response within 7-10 days with a Th2 response and IgE synthesis [Vella, A. T. et al., *J. Immunol.* 148 (1992) 2283-2290]. Even after the intranasal administration of *S. mansoni* egg extract, systemic IgE production occurs in the mouse model [Okano, M. et al., *J. Immunol.* 163 (1999) 6712-6717]. It has so far not been achieved, however, to identify or isolate the active substances responsible for the pronounced IL-4-inducing capacity of *S. mansoni* eggs.

DETAILED DESCRIPTION OF THE INVENTION

In connection with the present invention, a method is now made available for the first time with which the isolation of IL-4-inducing substances from *S. mansoni* eggs and from eggs of other parasitic worms is possible.

The object of the invention is therefore a method for the isolation of an IL-4-inducing protein from parasitic worms in which egg antigen (EA) or extract from Th2-inducing or IgE-inducing stages of parasitic worms (EX) is dialysed against water and lyophilised, the lyophilised EA or EX is fractionated by means of cation exchange chromatography, the fractions that bring about IL-4 induction in the incubation of human basophilic granulocytes are pooled and concentrated, affinity chromatography is performed with NHS-activated Sepharose to which *Aleuria aurantia* agglutinin is linked, the fractions that bring about IL-4 induction in the incubation of human basophilic granulocytes are pooled and concentrated. The protein obtained is preferably lyophilised subsequently.

According to a preferred embodiment of the invention, EA from *Schistosoma mansoni, Schistosoma japonicum, Schistosoma haematobium, Fasciola hepatica, Dicrocoelium lanceolatum, Echinococcus multilocularis, Ascaris lumbricoides, Ascaris suum, Ankylostoma duodenale, Necator americanus, Trichuris trichiura, Brugia malayi, Onchocerca volvulus, Wuchereria bancrofti, Taenia solium, Taenia bovis* and related species is used.

As an alternative to *A. aurantia* agglutinin, monoclonal antibodies to the proteins and polypeptides according to the invention (protein and carbohydrate components) are produced that are used for the purification of related molecules of other worm species.

These monoclonal antibodies are also used for immunohistological investigations, for example for the localisation of the proteins and polypeptides according to the invention and molecules derived therefrom in the parasite or to characterise the interaction of these proteins, polypeptides or derived molecules with host cells. Furthermore, these antibodies—possibly in humanised form—may be used for the biological neutralisation of the effect of the said proteins, polypeptides and molecules derived therefrom or molecules related thereto (such as allergens) in vitro and in vivo (the latter in conditions of unwanted Th2/IgE immune response).

According to a particular embodiment of the invention, the lyophilised EA or EX is taken up in 20 mM potassium phosphate buffer at a pH of 5.0 for the cation exchange chromatography. According to another particular embodiment of the invention, after pooling and concentration, the buffer of the active fractions obtained from cation exchange chromatography is exchanged to 50 mM sodium phosphate buffer, pH 7.0, before the affinity chromatography is performed.

Where *Schistosoma mansoni* egg antigen (SmEA) is used, a protein designated as IPSE is obtained in this way which has the amino acid sequence shown in SEQ ID NO: 2. The protein is preferably glycosylated; even in unglycosylated form, however, it has marked IL-4-inducing properties.

"SEQ ID NO" is for the present purposes understood to mean the numbering according to the numeric reference <400> used in WIPO standard ST.25.

The present invention further relates to proteins or polypeptides, that are homologues, derivatives or fragments of the proteins and polypeptides according to the invention and in particular of IPSE that likewise have the activity to stimulate the production of IL-4 and/or IL-13 in human basophilic granulocytes. The term 'homologues' should for the present purposes be understood to mean such proteins or polypeptides that have one or more amino acid exchanges with respect to the sequence represented in SEQ ID NO: 2; the term 'derivatives' should be understood to mean molecules in which individual amino acids are for example replaced by non-natural (artificial) amino acids or amino acids in the D form.

It has been proposed by Okano et al. that the carbohydrate components of *S. mansoni* egg antigen (SmEA) downregulate Th1 responses and are also necessary for SmEA-stimulated Th2 induction (cf. Velupillai, P. et al., *Proc. Natl. Acad. Sci, USA* 91 (1994) 18-22, Okano et al., *J. Immunol.* 163 (1999) 6712-6717). The authors adduced evidence from a mouse model in connection with intranasal sensitisation with deglycosylated (periodate-treated) SmEA which—unlike native egg antigen—was not able to induce IL-4, IL-5, IL-10 and SmEA-specific IgE production. It was further established that lacto-N-fucopentaose III, a predominant glycan component of SmEA that contains Lewis$^x$ (LE$^x$), acts as Th2-inducing adjuvant in mice when covalently bound to human serum albumin (M. Okano et al., *J. Immunol.* 167 (2001) 442-450).

In connection with the present invention, it was established that the proteins and polypeptides according to the invention, particularly IPSE, are also functionally effective in the absence of carbohydrates, i.e. in unglycosylated form. In particular, unglycosylated, recombinant IPSE displays a strong IL-4-inducing effect. The results obtained in connection with the present invention do not, however, exclude the possibility that carbohydrates contribute to a Th2 bias, which might include cell types other than basophils that are not activated by fucopentaose III-coupled human serum albumin.

Included according to the invention are therefore furthermore the aforesaid proteins or polypeptides in unglycosylated form as it has been established that these display an equally efficacious IL-4-inducing effect as their glycosylated analogues.

The invention further relates to a nucleic acid molecule that displays a nucleic acid sequence coding for a protein or polypeptide mentioned above. According to a particular embodiment of the invention, the nucleic acid molecule have the nucleic acid sequence shown in SEQ ID NO: 1.

Advantages of the Invention:

The proteins and polypeptides according to the invention lead, even in very low concentrations, to the release of the cellular messenger substances interleukin-4 (IL-4) and interleukin-13 (IL-13) from basophilic granulocytes (white blood cells) of non-sensitised healthy blood donors. IL-4 and IL-13 are key factors in the development of immunoglobulin-E-mediated (IgE-mediated) allergy. The proteins according to the invention play a central role in the initiation of type 2 T-helper cell response (Th2 response) and in the synthesis of IgE that is typical of parasitic worms. As Th2-inducing factors inhibit the development of a Th1 response (cellular immune response), the highly potent molecules of the present invention can be used immunopharmacologically, for example in diseases accompanied by a pathological Th1 response, such as multiple sclerosis.

The subject matter of the invention is therefore the use of the protein or polypeptide according to the invention for the production of a pharmaceutical composition for immunomodulation, preferably for the production of a pharmaceutical composition for the stimulation of IL-4 and/or IL-13 production or for the production of a pharmaceutical composition for the stimulation of IgE production.

The induction or amplification of a Th2-accentuated immune response is also desirable in view of the development of certain vaccines. Thus, a Th2 response is protective in certain parasitic worm infections (e.g. in nematode infections or *schistosomiasis*), while a Th1-accentuated immune response has the opposite effect here. This should be borne in mind in the production of anthelmintic and other vaccines.

Investigations concerning the mechanism of action have shown that basophil activation (degranulation, histamine, IL-4 and IL-13 release) by IPSE requires the presence of IgE at the surface of the basophils. This was shown by so-called IgE stripping and IgE resensitisation experiments in which receptor-bound IgE is dissociated by short-term low pH-treatment of the basophils, and the cells are then again loaded with IgE. The IgE dependence of IL-4 induction gives rise to the supposition that IPSE is effective as a result of binding and cross-linking of receptor-bound IgE.

In order to test whether IPSE is an immunoglobulin-binding factor, Western and dot blotting techniques were employed, with IPSE or IgE being fixed to nitrocellulose membrane by means of blotting and IPSE or IgE, respectively, being added in the soluble phase. Under both conditions, binding occurred between IgE and IPSE. Initial investigations with the Biacore method (Surface Plasmon resonance; Amersham Pharmacia Biotech, Freiburg, Germany) confirmed this finding, with high binding affinity between IPSE and IgE being demonstrated. In order to determine whether the immunoglobulin-binding activity of IPSE is restricted to the IgE isotype or affects other immunoglobulin classes as well, Western blotting investigations were conducted with IgG from sera from healthy northern European blood donors. It turned out in this context that IPSE also binds human IgG subclasses 1-4. Interestingly, competitive inhibition experiments revealed that IPSE binds to IgE with about 100 times higher affinity than to IgG.

In addition, IPSE binds to all peptide fragments of IgG after papain digestion, i.e. both to Fab and above all to Fc fragments.

Owing to its properties as an immunoglobulin-binding factor, the polypeptides according to the invention, particularly IPSE, can therefore be used for the detection and purification of immunoglobulins, particularly of IgE and IgG, and of fragments of the same (such as Fc and/or Fab fragments), for example in the performance of an ELISA (enzyme linked immunosorbent assay) or as part of affinity chromatography.

Owing to the immunological properties of the proteins and polypeptides of the invention, these are particularly suited for the production of a pharmaceutical composition for the induction or amplification of a Th2 immune response, particularly for the production of a pharmaceutical composition for the treatment of diseases accompanied by a Th1 immune response. These diseases are preferably diseases from the group consisting of multiple sclerosis, autoimmune uveitis, diabetes mellitus, rheumatoid arthritis, Behçet's syndrome, *Helicobacter pylori* infections, inflammatory intestinal diseases (particularly Crohn's disease), acute organ transplant rejection reaction and spontaneous recurrent abortions.

The object of the present invention is in particular the use of the polypeptides according to the invention, but above all IPSE, for the production of a pharmaceutical composition for immunomodulation, for example in allergic reactions. By virtue of its immunoglobulin-binding properties, the peptides according to the invention are furthermore suitable for the therapy of diseases that are characterised by an elevated serum IgE level and/or increased production of interferon gamma, such as for example allergic rhinoconjunctivitis and allergic bronchial asthma.

Also included are pharmaceutical compositions that contain a protein or polypeptide according to the invention together with pharmaceutically acceptable auxiliary substances and carriers.

The proteins and polypeptides of the present invention further serve to induce or intensify IL4, IL-13 and/or IgE production in vitro, wherein human basophilic granulocytes, B cells, T cells or natural killer (NK) cells in particular, though also other cells (of the immune system or other tissues, such as for example endothelial cells or fibroblasts) and cell lines derived therefrom, are incubated with an aforesaid protein or polypeptide. Thus, the proteins and polypeptides are suited for the production of IL-4 and/or IL-3 in vitro. In this method, the aforesaid cells are incubated with the protein or polypeptide and IL-4 and/or IL-13 are then isolated from the culture supernatant.

A further use of the proteins and polypeptides according to the invention consists in the inhibition of Th1 cytokine production/Th1 response by mononuclear cells from peripheral blood (from humans and animals) in vitro.

As the aforesaid nucleic acid molecules code for the proteins and peptides according to the invention, they are suitable as matrices for the in vitro production of the proteins or polypeptides, i.e. for in vitro expression. To this end, the DNA is for example incorporated in an expression vector and the corresponding proteins are overexpressed in recombinant fashion in suitable host cells, such as for example *Escherichia coli*. If glycolysation is critical for the functional activity of the proteins or polypeptides, expression takes place in the baculovirus or another eukaryontic system.

Therefore, the object of the invention is furthermore an expression vector that incorporates a built-in nucleic acid molecule.

The nucleic acid molecules are further suitable for the production of a pharmaceutical composition for in vivo expression (e.g. DNA vaccination). The production of the aforesaid proteins and polypeptides can therefore also take place in vivo, more specifically in view of a change in immune response. To this end, the corresponding DNA is incorporated in a gene transfer vector (such as for example an adenoviral vector). Thus, for example, adenoviral expression systems lead to transient, very high protein production; organ-specific expression is also possible. As a result of intramuscular injection of the vector, local protein or polypeptide production can be induced-initially in experimental animals. Suitable expression systems, particularly for use in humans, are well-known to the person skilled in the art and are continuously improved in terms of their safety in use.

The object of the invention is therefore also a gene transfer vector in which a nucleic acid molecule according to the invention is incorporated and also a pharmaceutical compound that contains such a gene transfer vector together with pharmaceutically acceptable auxiliary substances and/or carriers.

By means of examples of implementation, the invention is explained in greater detail below.

EXAMPLE 1

Method for the Extraction of *Schistosoma mansoni* Egg Antigen (SmEA)

The starting material for the purification of IPSE consists of eggs of *Schistosoma mansoni*, which are available in only a limited quantity as their extraction is costly and expensive. A total extract, so-called *Schistosoma mansoni* egg antigen (SmEA), was obtained from the schistosome eggs by extraction in phosphate-buffered saline solution (Boros D L et al., *J. Exp. Med.* 132 (1970) 488-507; Carter C E et al., *J Parasitol.* 64 (1978) 285-290). Following dialysis against distilled water, this was stored in lyophilised form for further processing. As IPSE is present in SmEA only in very low concentration, it is not detectable among the numerous constituents following representation of the total extract by SDS-PAGE and silver staining.

EXAMPLE 2

Method for the Purification of IPSE From SmEA

A. Cation Exchange Chromatography:

Unlike other methods for protein purification such as exclusion chromatography (Superdex 200 PC, SMART system, Pharmacia), hydrophobic interaction chromatography (HIC), Reversed Phase HPLC and preparative isoelectrofocussing (Rotofor, Bio-Rad Laboratories, Munich, Germany), which in our hands led to considerable to total loss and/or unsatisfactory enrichment of the IL-4-inducing active principle, we managed to achieve clear enrichment of IPSE with the technique of cation exchange chromatography.

To this end, lyophilised SmEA (2 mg) was taken up in 0.5 ml 20 mM potassium phosphate buffer, pH 5.0, and separated by means of cation exchange chromatography (SP-Sepharose; prepacked 1 ml HiTrap® columns, Amersham Pharmacia, Freiburg, Germany). Following application of the sample and washing with starting buffer (20 mM K phosphate buffer, pH 5.0), bound material was eluted with a linear salt gradient to 1M KCl in starting buffer. Separatation took place on an Äktaprime system (Amersham Pharmacia, Freiburg, Germany) with a flow rate of the solvent of 1 ml/min. Fractions of 0.5 ml were collected. The pH of 5.0 is critical since at higher pH values (pH 6.0) a large proportion of IPSE leaves the column together with the protein-rich effluent and therefore enrichment of the active principle does not occur. The functionally active fractions (detection via determination of IL-4 induction in the basophil test, see below) were then pooled and concentrated via Centricon Plus-20 (Millipore, Eschbom, Germany) and the buffer was exchanged to 50 mM sodium phosphate buffer, pH 7.0. The use of Centricon Plus20 for concentration was critical for the yield of IPSE since loss of the active principle of more than 90% occurred with the use of other concentration units such as for example Centricon and Centriprep. In order to reduce even further the losses due to concentration with Centricon Plus20, the units were additionally preincubated with 5% Tween 20 overnight. Prior to use, they were then rinsed thoroughly with plenty of double-distilled water to avoid the transfer of Tween into the functional assays and thus damage to the basophils with the consequence of falsely negative results. This procedure made it possible to keep the loss of IL-4-inducing activity in connection with the evaporation procedure below 50%.

Following concentration of the samples (by a factor of at least 5), it was managed to detect two adjoining bands in the molecular weight range around 40 kD in the active fractions, in addition to irrelevant components in SDS PAGE gel after silver staining. However, a longer development period for silver staining (at least 30 minutes) was required for the detection of these two bands. In the non-active fractions, the double bands were not detectable.

The suspicion that one (or both) of the two bands was the active principle sought was supported by the result of the following experiment: fractionation of SMEA via SDS-PAGE and fractionated electroelution of the gel allowed to assign the IL-4-inducing activity to the molecular weight range around 40 kD, i.e. the range in which both bands were to be found.

B. Affinity Chromatography via *Aleuria aurantia* agglutinin Sepharose:

The fact that schistosome eggs contain numerous, in some cases unusually glycolysated glycoproteins and glycolipids was used for further purification. Accordingly, affino blot analysis showed that the components of the schistosome egg total extract following separation via SDS-PAGE and transfer to nitrocellulose membrane, were differentially recognised by a number of labelled lectins, including *Aleuria aurantia* agglutinin, Concanavalin A, *Datura stramonium* agglutinin, *Galanthus nivalis* agglutinin, *Maackia amurensis* agglutinin, peanut agglutinin, *Ricinus communis* agglutinin, *Sambucus nigra* agglutinin, wheat germ agglutinin. Only three lectins reacted, on the other hand, with the active fractions following cation exchange chromatography. Of these, only *Aleuria aurantia* agglutinin, which binds to α1-6-glycosidically linked fucose, interacted selectively with the two adjoining bands around 40 kD. On the other hand, the two other lectins (peanut agglutinin and *Ricinus communis* agglutinin) reacted exclusively or additionally with other bands, including those detectable in non-active fractions.

The working hypothesis was therefore put forward that the double bands correspond to IPSE, and as the next step an affinity chromatography was performed with *Aleuria aurantia* agglutinin (Vector Laboratories, Alexis-Deutschland GmbH, Grünberg, Germany). To this end, this lectin was coupled to NHS-activated Sepharose (HiTrap column; Amersham Pharmacia). Coupling was carried out in accordance with the manufacturer's recommendations. For the purposes of the affinity chromatography, the functionally active fractions from the cation exchange chromatography were transferred to the column, washed with starting buffer (50 mM sodium phosphate buffer, pH 7.0) and eluted with elution buffer (starting buffer +0.1 M fucose (Sigma, Taufkirchem, Germany)). The fractions were then again concentrated by means of Centricon Plus 20 (Millipore GmbH, Eschborn, Germany), as described above, and the produced material was again characterised with the aid of SDS-PAGE and subsequent silver staining or subsequent affinoblotting with labelled *A. aurantia* agglutinin. The IL-4-inducing activity was located exclusively in the fractions with the *A. aurantia* agglutinin-binding double bands. The positive fractions were pooled and aliquotted or dialysed against double-distilled water and lyophilised. Storage was at −80° C.

EXAMPLE 3

Determination of the Complete Nucleotide and Amino Acid Sequence of IPSE

A. N-Terminal Partial Sequencing of IPSE:

To prepare adequate quantities of IPSE for N-terminal sequencing, the active fractions from 10 cation exchange chromatography runs were pooled and further purified via *Aleuria aurantia* agglutinin affinity chromatography. The material thereby obtained (IPSE) was represented in SDS-PAGE (silver staining or lectin blot) at 40 kD as double bands without further contamination. The N-terminal partial sequencing of both bands (without further fractionation) permitted identification of 18 of the 20 N-terminal amino acids. The searching of protein databases did not reveal any currently known homologous proteins. Searching of an EST database produced an Expressed Sequence Tag (EST) from a *Schistosoma mansoni* egg cDNA bank ranking first. An amino acid sequence that was identical in 11 consecutive amino acids to the N-terminal IPSE sequence was derived from one of the three reading frames of this EST.

B. Isolation of cDNA for IPSE from *S. mansoni* Egg cDNA Banks

Figure 2:
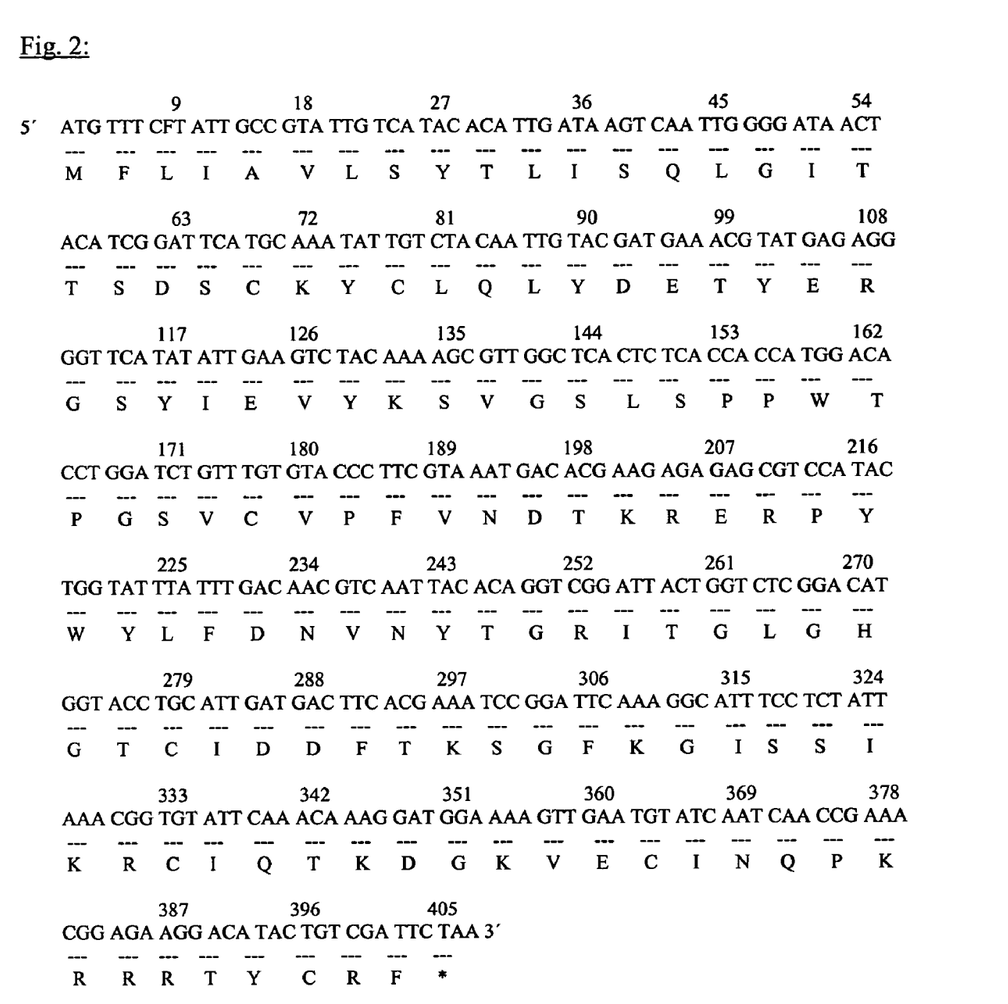
FIG. 2 shows the complete nucleotide and amino acid sequence of IPSE.

The sequence information described in the section above permitted the production of a specific (undegenerated) DNA probe for searching for the nucleotide sequence of IPSE in *Schistosoma mansoni* egg cDNA libraries. An *S. mansoni* egg cDNA library produced by us and also one produced by G. Oliveira (both in the λ zap vector) contained clones that reacted with this probe. Sequencing of these clones revealed that their entire N-terminal sequence is identical to the N-terminal sequence of IPSE, with both initially unknown amino acids being cysteines (the amino acid cysteine is hard to detect via N-terminal sequencing). A comparison of the sequence found in connection with the present invention with the EST indicated above revealed considerable differences that could possibly be attributed to errors in the sequencing and switches in the reading frame of the EST. FIG. 2 illustrates the complete sequence of IPSE at DNA level and also at protein level (with a leader sequence of 20 amino acids).

EXAMPLE 4

Detection System for IPSE

A. Purification and Stimulation of Human Basophilic Granulocytes:

The isolation and stimulation of human basophilic granulocytes was performed by the method of K. Haisch et al. (*J. Immunol. Methods* 226 (1999) 129-137). To this end, mononuclear cells were obtained from venous blood of healthy blood donors with the aid of a Ficoll-Percoll gradient, from which basophil-rich fractions were isolated via countercurrent elutriation. The basophils were isolated therefrom to a high level of purity (routinely more than 98% purity) by means of immunomagnetic beads (MACS system). The purified basophils were incubated with SmEA or its fractions for 4 hours (IL-4) or 18 hours (IL-13) and the supernatants taken off for cytokine determination and stored at −70° C. until the analysis.

B. IL-4 and IL-13 ELISA:

The concentrations of the cytokines IL-4 and IL-13 in the culture supernatant were determined by means of a sandwich ELISA (inter alia, commercially available).

EXAMPLE 5

Production of Polyclonal and Monoclonal Antibodies Against IPSE

To produce polyclonal antibodies, IPSE is injected intramuscularly in both thighs of rabbits in the presence of Titer-Max adjuvant. The formation of IPSE-specific antibodies is determined via Western blotting. Booster injections are carried out at 4-week intervals.

The production of monoclonal antibodies is performed in accordance with the method developed by Köhier and Milstein (*Nature* 256 (1975) 495-497) in the modification according to *Current Protocols of Immunology* (Editors: J. E. Coligan et al., publisher: John Wiley & Sons, Inc. (1997); ISBN: 0-471-522767). To this end, IPSE is injected intraperitoneally into two mice in the presence of adjuvant. A booster injection (without adjuvant) is carried out after 10-14 days. 3 days letter, the spleen cells of the mice are fused with myeloma cell line SP2/0-Ag14. On the next day, hypoxanthine-aminopterinthymidine (HAT) containing medium is added for the selection of hybridoma cells. After 10-14 days, screening of the primary hybridoma supernatants for reactivity of antibodies to IPSE is performed by the Western blot method. Candidate hybridoma lines are propagated and (re) cloned by Limiting Dilution.

EXAMPLE 6

Effectiveness of Unglycosylated IPSE

Lacto-N-fucopentaose III (LNFPIII) is a main glycan component of glycoproteins in *S. mansoni* egg antigen extracts. In the light of the capacity of the polypeptides according to the invention, particularly of IPSE, to activate human basophils, it was therefore investigated whether lacto-N-fucopentaose III (LNFPIII-HSA) (Biocarb Chemicals, Lund, Sweden) bound to human serum albumin was also capable of activating basophils. The experimental method corresponded to the method referred to in example 4 A.

It was established that, unlike the *S. mansoni* egg antigen used as a positive control, LNFPIII-HSA did not induce degranulation of basophils, release of mediators or expression of IL-4 or IL-13 over a wide concentration range (0.03-30 µg/ml).

EXAMPLE 7

Investigation of Immunoglobulin-Binding Characteristics of IPSE

Western and dot blotting techniques were used for the investigation of immunoglobulin-binding properties of the polypeptides according to the invention, particularly IPSE.

Dot blotting: Polyclonal IgE (BA1004; DPC Biermann, Bad Nauheim, Germany) was applied to nitrocellulose membrane in various quantities (1000-30 ng/dot). Free binding sites of the membrane were then blocked by incubation in 0.1 M Tris-buffered saline solution, pH 7.4, with the addition of 0.05% (v/v) Tween 20 (Tris-Tween) and the membrane was incubated overnight at RT with biotinylated recombinant IPSE (His tag fusion protein; 1 µg/ml). After washing, the blots were incubated for 2 hours with streptavidine-alkaline phosphatase (1:5000). Development of the blots was carried out after renewed washing by the addition of the substrate chromogen mixture (nitro blue tetrazolium-bromo chloro indolyl phosphate).

In parallel, various quantities of His tag IPSE fusion protein (1000-30 ng/dot) were applied to nitrocellulose membrane. Following the blocking of free binding sites (see foregoing paragraph), the membrane was incubated overnight at RT with biotinylated polyclonal IgE (1 µg/ml). Further development was carried out via streptavidine-alkaline phosphatase as in the previous paragraph.

Western blotting: To this end, natural IPSE or recombinant His tag IPSE fusion protein were fractionated by means of SDS-PAGE (12% T, 4% C) by a standard method (Lämmli, U. K., *Nature* 227 (1970) 680-685) under non-reducing conditions and transferred by means of semidry blotting (30 minutes, 0.8 mA/cm) to nitrocellulose membrane (Schleicher & Schüll, Dassel, Germany). Free protein binding sites were blocked by incubation of the membrane in Tris-Tween. Strips of the membrane were then incubated overnight at RT with sera of healthy, unsensitised blood donors (1:20 and 1:100 in Tris-Tween). Following washing, the strips were incubated for 2 hours at RT with alkaline phosphatase-labelled anti-human IgE (1:2000 in Tris-Tween; Allergopharma, Reinbek, Germany) or anti-human IgE (1:40 000; Dianova, Hamburg, Germany). Development of the blots was carried out after renewed washing by addition of the substrate chromogen mixture (nitro blue tetrazolium-bromo chloro indolyl phosphate).

In order to compare the affinity of binding of IPSE to IgE or to IgG, Western blots of His tag IPSE (0.5 µg/cm) were incubated with human IgE (100-100,000 ng/ml). Detection of IgE binding to His tag IPSE was carried out by incubation with alkaline phosphatase-labelled anti-human IgE (1:2000; Allergopharma, Reinbek, Germany).

It was established that IPSE binds to human IgG subclasses 1 to 4 and, to Fc and Fab fragments after papain digestion, and also—with around 100 times higher affinity than to IgG—to IgE.

The invention claimed is:

1. An isolated protein or polypeptide having the amino acid sequence shown in SEQ ID NO: 2.

2. An isolated nucleic acid molecule encoding a protein or polypeptide according to claim 1.

3. An expression vector comprising the nucleic acid molecule according to claim 2.

4. An isolated nucleic acid molecule encoding a protein or polypeptide having the amino acid sequence shown in SEQ ID NO: 2, wherein the nucleic acid sequence is shown in SEQ ID NO: 1.

5. An isolated nucleic acid molecule of claim 4, wherein the protein or polypeptide coded by the nucleic acid is glycosylated.

6. An expression vector comprising the nucleic acid molecule according to claim 4.

7. An expression vector comprising the nucleic acid molecule according to claim 5.

8. A pharmaceutical composition comprising a protein or polypeptide with the amino acid sequence shown in SEQ ID NO: 2 together with pharmaceutically acceptable auxiliary substances and carriers.

9. A pharmaceutical composition of claim 8, wherein the protein or polypeptide is glycosylated.

10. A method of stimulating IL-4 and/or IL-13 production comprising administering a pharmaceutical composition comprising a protein or polypeptide having the amino acid sequence shown in SEQ ID NO: 2.

11. The method of claim 10 wherein the protein or polypeptide is glycosylated.

12. A method of stimulating IgE production comprising administering a pharmaceutical composition comprising the protein or polypeptide having the amino acid sequence shown in SEQ ID NO: 2.

13. The method of claim 12 wherein the protein or polypeptide is glycosylated.

14. A method of inducing or amplifying a Th2 immune response comprising administering a pharmaceutical composition comprising the protein or polypeptide having the amino acid sequence shown in SEQ ID NO: 2.

15. A method of inducing or amplifying IL-4, IL-13 and/or IgE production in vitro comprising incubating cells from the group consisting of human basophilic granulocytes, B cells, T cells NK cells, endothelial cells and fibroblasts and other cells of the immune system or other tissues and cell lines derived therefrom with a protein or polypeptide having the amino acid sequence shown in SEQ ID NO: 2.

16. A method of detecting and purifying immunoglobulins or fragments thereof that bind to SEQ ID NO:2, comprising contacting said immunoglobulins or fragments thereof with the protein or polypeptide having the amino acid sequence shown in SEQ ID NO: 2; detecting binding between the polypeptide of SEQ ID NO: 2 and immunoglobulins or fragments thereof and purifying the bound immunoglobulins or fragments thereof.

17. A method of expressing proteins or polypeptides in vitro comprising incorporating the nucleic acid molecule of claim 4 or 2 into a suitable expression vector wherein the proteins or polypeptides are recombinantly overexpressed in suitable host cells.

18. The method according to claim 17, wherein the host cells are *Escherichia coli*, baculovirus or eukaryotic cells.

19. A composition comprising a vector comprising the nucleic acid molecule according to claim 4 or 2 and pharmaceutically acceptable auxiliary substances and/or carriers.

20. A method for the isolation of a protein having the amino acid sequence shown in SEQ ID NO: 2 comprising
   a) dialyzing *Schistosoma mansoni* egg antigen (SmEA) against water;
   b) lyophilizing the dialyzed SmEA;
   c) separating the lyophilized SmEA by cation exchange chromatography and collecting fractions;
   d) testing the fractions for IL-4 induction during incubation with human basophilic granulocytes;
   e) pooling and concentrating the fractions that bring about IL-4 induction;
   f) performing affinity chromatography of the concentrate with NHS-activated Sepharose to which Aleuria aurantia agglutinin or monoclonal antibodies to a protein having the amino acid sequence shown in SEQ ID NO: 2 are linked and collecting the fractions; and
   g) testing the fractions that bring about IL-4 induction during incubation with human basophilic granulocytes
   h) pooling and concentrating the fractions that bring about IL-4 induction.

21. The method according to claim 20 wherein the isolated protein is subsequently lyophilized.

\* \* \* \* \*

UNITED STATES PATENT AND TRADEMARK OFFICE
CERTIFICATE OF CORRECTION

PATENT NO. : 7,601,812 B2  Page 1 of 1
APPLICATION NO. : 10/469499
DATED : October 13, 2009
INVENTOR(S) : Schramm et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1177 days.

Signed and Sealed this

Fifth Day of October, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 405
<212> TYPE: DNA
<213> ORGANISM: Schistosoma mansoni
<220> FEATURE:
<221> NAME/KEY: CDS
<222> LOCATION: (1)...(405)

<400> SEQUENCE: 1 atg ttt ctt att gcc gta ttg tca tac aca ttg ata agt caa ttg ggg      48
Met Phe Leu Ile Ala Val Leu Ser Tyr Thr Leu Ile Ser Gln Leu Gly
 1               5                  10                  15 ata act aca tcg gat tca tgc aaa tat tgt cta caa ttg tac gat gaa      96
Ile Thr Thr Ser Asp Ser Cys Lys Tyr Cys Leu Gln Leu Tyr Asp Glu
            20                  25                  30 acg tat gag agg ggt tca tat att gaa gtc tac aaa agc gtt ggc tca     144
Thr Tyr Glu Arg Gly Ser Tyr Ile Glu Val Tyr Lys Ser Val Gly Ser
        35                  40                  45 ctc tca cca cca tgg aca cct gga tct gtt tgt gta ccc ttc gta aat     192
Leu Ser Pro Pro Trp Thr Pro Gly Ser Val Cys Val Pro Phe Val Asn
    50                  55                  60
```

```
gac acg aag aga gag cgt cca tac tgg tat tta ttt gac aac gtc aat    240
Asp Thr Lys Arg Glu Arg Pro Tyr Trp Tyr Leu Phe Asp Asn Val Asn
 65              70                  75                  80 tac aca ggt cgg att act ggt ctc gga cat ggt acc tgc att gat gac    288
Tyr Thr Gly Arg Ile Thr Gly Leu Gly His Gly Thr Cys Ile Asp Asp
             85                  90                  95 ttc acg aaa tcc gga ttc aaa ggc att tcc tct att aaa cgg tgt att    336
Phe Thr Lys Ser Gly Phe Lys Gly Ile Ser Ser Ile Lys Arg Cys Ile
            100                 105                 110 caa aca aag gat gga aaa gtt gaa tgt atc aat caa ccg aaa cgg aga    384
Gln Thr Lys Asp Gly Lys Val Glu Cys Ile Asn Gln Pro Lys Arg Arg
            115                 120                 125 agg aca tac tgt cga ttc taa                                        405
Arg Thr Tyr Cys Arg Phe *
    130

<210> SEQ ID NO 2
<211> LENGTH: 134
<212> TYPE: PRT
<213> ORGANISM: Schistosoma mansoni

<400> SEQUENCE: 2

Met Phe Leu Ile Ala Val Leu Ser Tyr Thr Leu Ile Ser Gln Leu Gly
 1               5                  10                  15

Ile Thr Thr Ser Asp Ser Cys Lys Tyr Cys Leu Gln Leu Tyr Asp Glu
             20                  25                  30

Thr Tyr Glu Arg Gly Ser Tyr Ile Glu Val Tyr Lys Ser Val Gly Ser
         35                  40                  45

Leu Ser Pro Pro Trp Thr Pro Gly Ser Val Cys Val Pro Phe Val Asn
     50                  55                  60

Asp Thr Lys Arg Glu Arg Pro Tyr Trp Tyr Leu Phe Asp Asn Val Asn
 65              70                  75                  80

Tyr Thr Gly Arg Ile Thr Gly Leu Gly His Gly Thr Cys Ile Asp Asp
             85                  90                  95

Phe Thr Lys Ser Gly Phe Lys Gly Ile Ser Ser Ile Lys Arg Cys Ile
            100                 105                 110

Gln Thr Lys Asp Gly Lys Val Glu Cys Ile Asn Gln Pro Lys Arg Arg
            115                 120                 125

Arg Thr Tyr Cys Arg Phe
    130
```